(12) United States Patent
Paris et al.

(10) Patent No.: US 9,421,596 B2
(45) Date of Patent: Aug. 23, 2016

(54) BENDING INSTRUMENT AND METHODS OF USING SAME

(71) Applicant: University of Alaska Anchorage, Anchorage, AK (US)

(72) Inventors: Anthony James Paris, Anchorage, AK (US); Shawn Wooten, Anchorage, AK (US); Paul Harren, Anchorage, AK (US); Wesley Burgess, Anchorage, AK (US)

(73) Assignee: University of Alaska Anchorage, Anchorage, AK (US)

( * ) Notice: Subject to any disclaimer, the term of this patent is extended or adjusted under 35 U.S.C. 154(b) by 0 days.

(21) Appl. No.: 14/688,770

(22) Filed: Apr. 16, 2015

(65) Prior Publication Data

US 2015/0298192 A1 Oct. 22, 2015

Related U.S. Application Data

(60) Provisional application No. 61/980,139, filed on Apr. 16, 2014.

(51) Int. Cl.
| | | |
|---|---|---|
| *B21D 7/024* | (2006.01) | |
| *B21D 7/06* | (2006.01) | |
| *B21F 1/00* | (2006.01) | |
| *A61B 17/88* | (2006.01) | |
| *A61B 17/70* | (2006.01) | |

(52) U.S. Cl.
CPC ............ *B21D 7/024* (2013.01); *A61B 17/8863* (2013.01); *B21D 7/063* (2013.01); *B21F 1/002* (2013.01); *A61B 17/7011* (2013.01)

(58) Field of Classification Search
CPC .......... B21D 7/02; B21D 7/022; B21D 7/024; B21D 7/06; B21D 7/063; B25B 7/12; B25B 7/123; B21F 1/002; A61B 17/7002; A61B 17/7074; A61B 17/8863
See application file for complete search history.

(56) References Cited

U.S. PATENT DOCUMENTS

| | | |
|---|---|---|
| 1,762,234 A | 6/1930 | Matthews |
| 3,447,353 A | 6/1969 | Noveske |
| 3,662,580 A | 5/1972 | Power |
| 3,785,190 A | 1/1974 | Schall et al. |
| 4,052,879 A | 10/1977 | Crees |
| 4,428,216 A | 1/1984 | Fling |
| 4,587,824 A | 5/1986 | Wierseman et al. |
| 4,608,888 A | 9/1986 | Rommel |
| 4,785,650 A | 11/1988 | Lusty |

(Continued)

OTHER PUBLICATIONS

ASTM Standard F136, 2002a, "Standard Specification for Wrought Titanium—4Aluminum—4Vanadium Extra Low Interstitial Allow for Surgical Implant Applications," ASTM International, West Conshohocken, PA, 2003, DOI: 10.1520/C0033-03A, www.astm.org (4 pages).

(Continued)

*Primary Examiner* — Debra Sullivan
(74) *Attorney, Agent, or Firm* — Ballard Spahr LLP

(57) ABSTRACT

Bending instruments for selectively applying a bending force to a rod or rod-like element, such as for example and without limitation, a surgical rod. Exemplary bending instruments include a first handle, a second handle, and a gear assembly. Pivotal movement of the second handle relative to the first handle effects a corresponding movement of the gear assembly components to thereby effect bending of the rod or rod-like element.

20 Claims, 14 Drawing Sheets

(56) References Cited

U.S. PATENT DOCUMENTS

| | | | |
|---|---|---|---|
| 4,986,104 A | 1/1991 | Caporusso et al. | |
| 5,389,099 A | 2/1995 | Hartmeister et al. | |
| 5,431,035 A | 7/1995 | Sheen | |
| 5,490,409 A | 2/1996 | Weber | |
| 5,548,985 A | 8/1996 | Yapp | |
| 6,035,691 A | 3/2000 | Lin et al. | |
| 7,234,338 B2 | 6/2007 | Mirtz et al. | |
| 7,302,887 B1 | 12/2007 | Chapman et al. | |
| 7,454,939 B2 | 11/2008 | Garner et al. | |
| 9,003,859 B2 | 4/2015 | Paris | |
| 2006/0150699 A1* | 7/2006 | Garner et al. | 72/31.04 |
| 2012/0247173 A1* | 10/2012 | Paris et al. | 72/362 |
| 2014/0066994 A1* | 3/2014 | Dominik et al. | 606/281 |

OTHER PUBLICATIONS

LaRusso, L. (2013). Spinal Fusion. Retrieved Jan. 4, 2013, from CVS Pharmacy Health Resources:http://health.cvs.com/GetContent.aspx?token=f75979d3-9c7c-4b16-af56-3e122-a3f19e3&chunkiid=102862 (6 pages).

Mohan Lalith, A., & Das, K. (2003). History of Surgery for the Correction of Spinal Deformity: Modern Era of Spinal Instrumentation. Retrieved Jan. 4, 2013, from www.medscape.com: http://www.medscape.com/viewarticle/448306.sub.--print (7 pages)

National Scoliosis Foundation. (2014). Instrumentation Systems for Scoliosis Surgery. Retrieved from http://www.scoliosis.org/resources/medicalupdates/instrumentationsystems.php (3 pages).

North America Spine Society (2009) Spinal Fusion. Retrieved Jan. 4, 2013, from http://www.knowyourback.org/Pages/Treatments/SugicalOptions/SpinalFu- sion.aspx (2 pages).

Paris, A.J. (2005). A study on the Biomechanical Behavior of Spinal Fixation assemblies with Stainless Steel and Titanium Rods in a Vertebrectomy Model Phase II: The Effect of Lordosis. Boise: Department of Mechanical Engineering Boise State University (148 pages).

The History of Lumbar Spine Stabilization. (n. d.). Retrieved Jun. 22, 2012, from The Burton Report: http://www.burtonreport.com/InfSpine/SurgStabilSpineHistory.htm (3 pages).

Thoraco-lumbar screw-rod unit (anterior) [Web Graphic]. Retrieved from http://www.medicalexpo.com/prod/life-spine/thoraco-lumbar-screw-rod-units-anterior-85015-549259.html (7 pages).

Restriction Requirement issued by the U.S. Patent & Trademark Office on Apr. 8, 2014 for U.S. Appl. No. 13/078,546, filed Apr. 1, 2011 and granted as U.S. Pat. No. 9,003,859 on Apr. 14, 2015 (Inventor—Paris, et al.) (8 pages).

Response to Restriction Requirement filed on Jun. 9, 2014 for U.S. Appl. No. 13/078,546, filed Apr. 1, 2011 and granted as U.S. Pat. No. 9,003,859 on Apr. 14, 2015 (Inventor—Paris, et al.) (9 pages).

Non-Final Office Action issued by the U.S. Patent & Trademark Office on Aug. 14, 2014 for U.S. Appl. No. 13/078,546, filed Apr. 1, 2011 and granted as U.S. Pat. No. 9,003,859 on Apr. 14, 2015 (Inventor—Paris, et al.) (11 pages).

Response to Non-Final Office Action filed on Dec. 15, 2014 for U.S. Appl. No. 13/078,546, filed Apr. 1, 2011 and granted as U.S. Pat. No. 9,003,859 on Apr. 14, 2015 (Inventor—Paris, et al.) (16 pages).

Notice of Allowance issued by the U.S. Patent & Trademark Office on Feb. 5, 2015 for U.S. Appl. No. 13/078,546, filed Apr. 1, 2011 and granted as U.S. Pat. No. 9,003,859 on Apr. 14, 2015 (Inventor—Paris, et al.) (7 pages).

Issue Notification issued by the U.S. Patent & Trademark Office on Mar. 25, 2015 for U.S. Appl. No. 13/078,546, filed Apr. 1, 2011 and granted as U.S. Pat. No. 9,003,859 on Apr. 14, 2015 (Inventor—Paris, et al.) (1 pages).

U.S. Appl. No. 61/980,139, filed Apr. 16, 2014, Paris (University of Alaska, Anchorage).

* cited by examiner

BENDING INSTRUMENT AND METHODS OF USING SAME

CROSS-REFERENCE TO RELATED PATENT APPLICATION

This application claims priority to and the benefit of the filing date of U.S. Provisional Patent Application No. 61/980,139, filed Apr. 16, 2014, which application is hereby incorporated herein by reference in its entirety.

FIELD

This invention relates to bending instruments and, more particularly, to bending instruments configured for one-handed operation.

BACKGROUND

The bending of rod-like elements is commonly used in a variety of applications. For example, in association with spinal surgeries, spinal rod implants are often bent to follow the unique curvature of a patient's spine. Existing rod benders generally require the use of two-hands. To prevent undesired movement of the rod during bending, it is often necessary for one individual to stabilize the rod while a second individual moves the rod bender in a desired fashion. In addition to these limitations, surgical rod benders are frequently table-mounted and, consequently, require a surgeon to leave the side of a surgical patient each time an adjustment to the bending angle of a surgical rod is required.

Thus, there is a need in the pertinent art for bending instruments that are configured for safe, efficient, and precise operation by a single user.

SUMMARY

Described herein, in one aspect, is a bending instrument having a first handle, a second handle, and a gear assembly. The first handle can have a proximal end and a distal base portion. The distal base portion can have a base surface and define a support member that projects from the base surface. The second handle can have a proximal end and a distal end, with the distal end being pivotally coupled to the distal base portion of the first handle. The gear assembly can comprise a driving gear, a compound gear, a driving pawl, and a locking pawl. The driving gear can be rotationally coupled to the distal base portion of the first handle and configured for rotation about a first rotational axis. The driving gear can have a first surface and define an inner bending member and an outer bending member that project from the first surface substantially parallel to the first rotational axis. The compound gear can be rotationally coupled to the distal base portion of the first handle and have a first gear portion and a second gear portion. The compound gear can be configured for common rotation about a second rotational axis. The second gear portion can be positioned between the distal base portion of the first handle and the first gear portion relative to the second rotational axis. The first gear portion can be positioned in engagement with the driving gear. The driving pawl can be pivotally coupled to the second handle proximate the distal end of the second handle. The driving pawl can be configured for selective engagement with the second gear portion of the compound gear. The locking pawl can be pivotally coupled to the distal base portion of the first handle and configured for selective engagement with the second gear portion of the compound gear to thereby prevent rotation of the compound gear about the common rotational axis. In operation, the support member of the first handle and the inner and outer bending members of the driving gear cooperate to define a rod receiving channel configured to receive a rod. Pivotal movement of the second handle relative to the first handle can effect a corresponding pivotal movement of the driving pawl, and the driving pawl can be configured to effect rotation of the compound gear to thereby rotate the driving gear.

In another aspect, described herein is a method of bending a rod-like element. The method can include positioning the rod-like element within a rod receiving channel of a bending instrument as disclosed herein. The method can further include selectively pivotally moving the second handle relative to the first handle to effect a corresponding pivotal movement of the driving pawl, wherein the driving pawl effects rotation of the compound gear to thereby rotate the driving gear.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE FIGURES

These and other features of the preferred embodiments of the invention will become more apparent in the detailed description in which reference is made to the appended drawings wherein.

Figure 3:
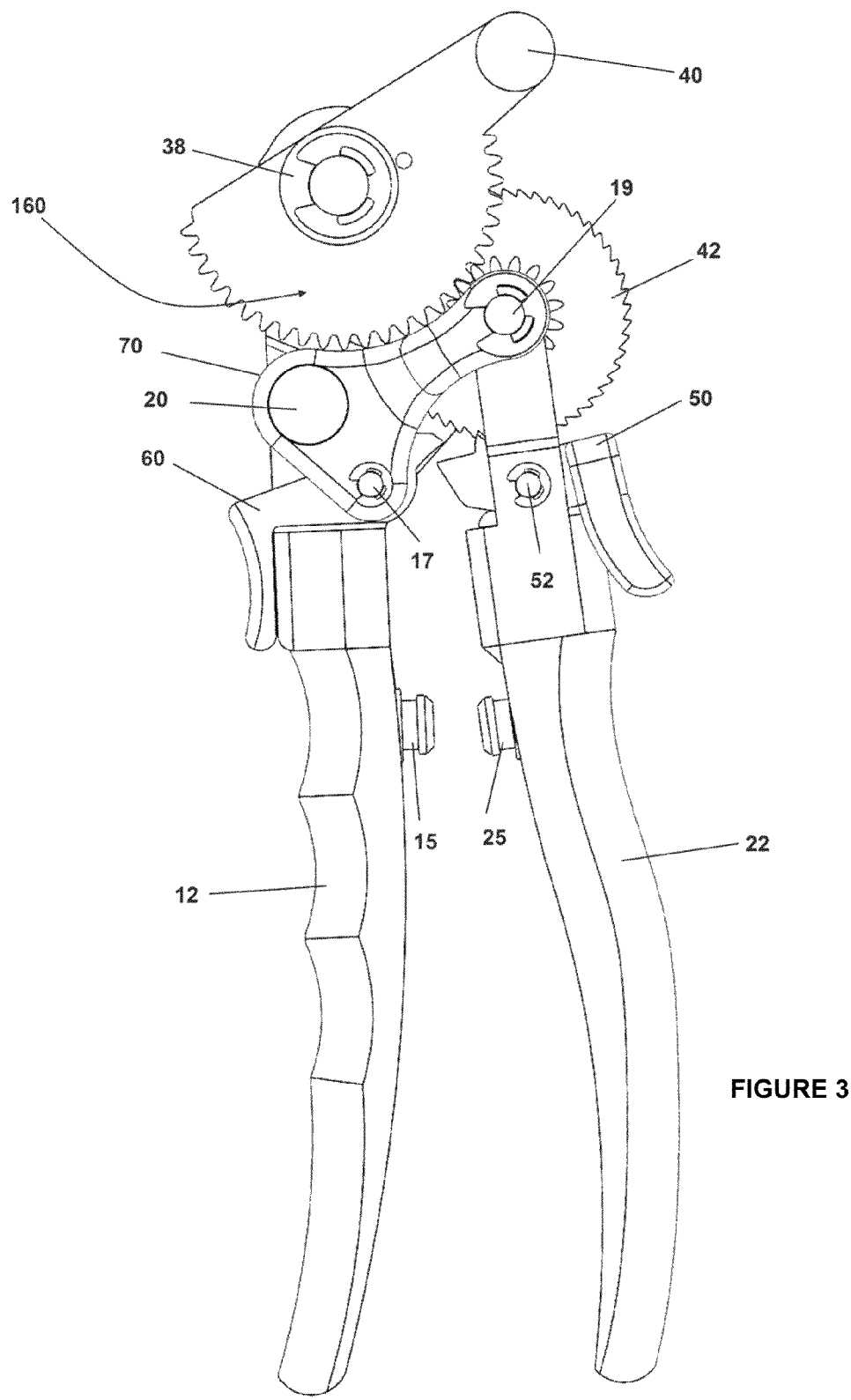
Figure 4:
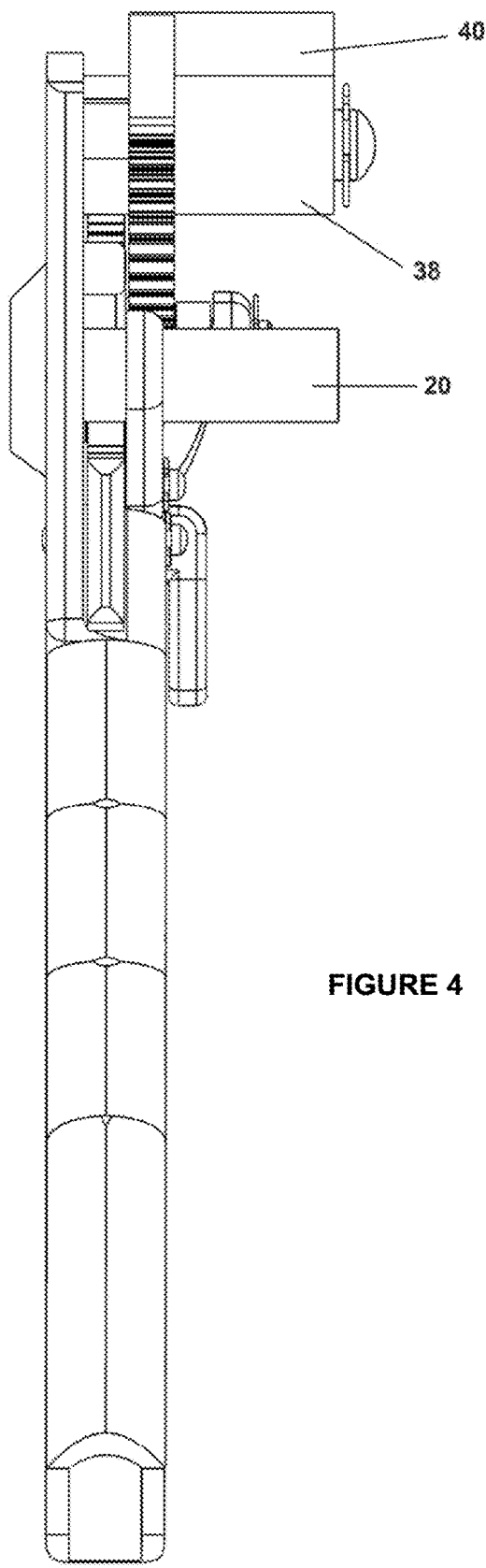
Figure 5:
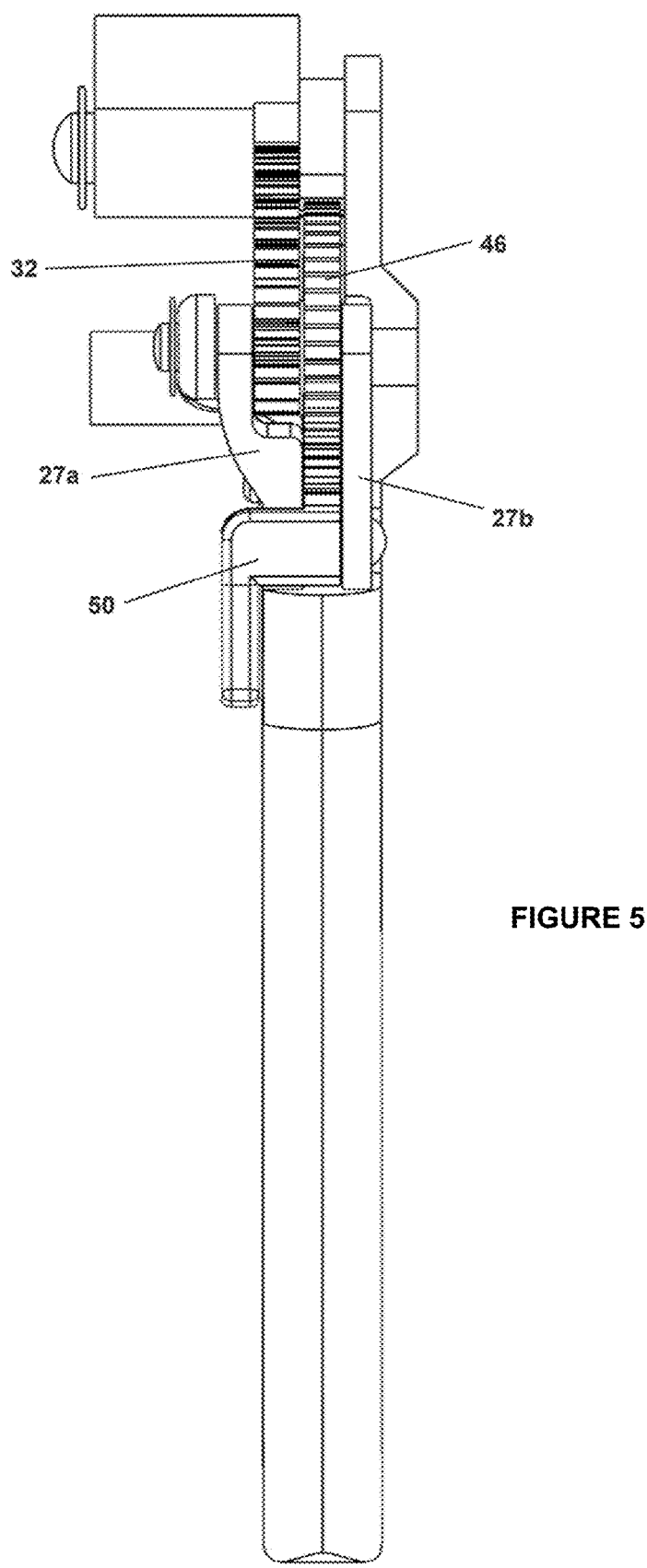
Figure 6:
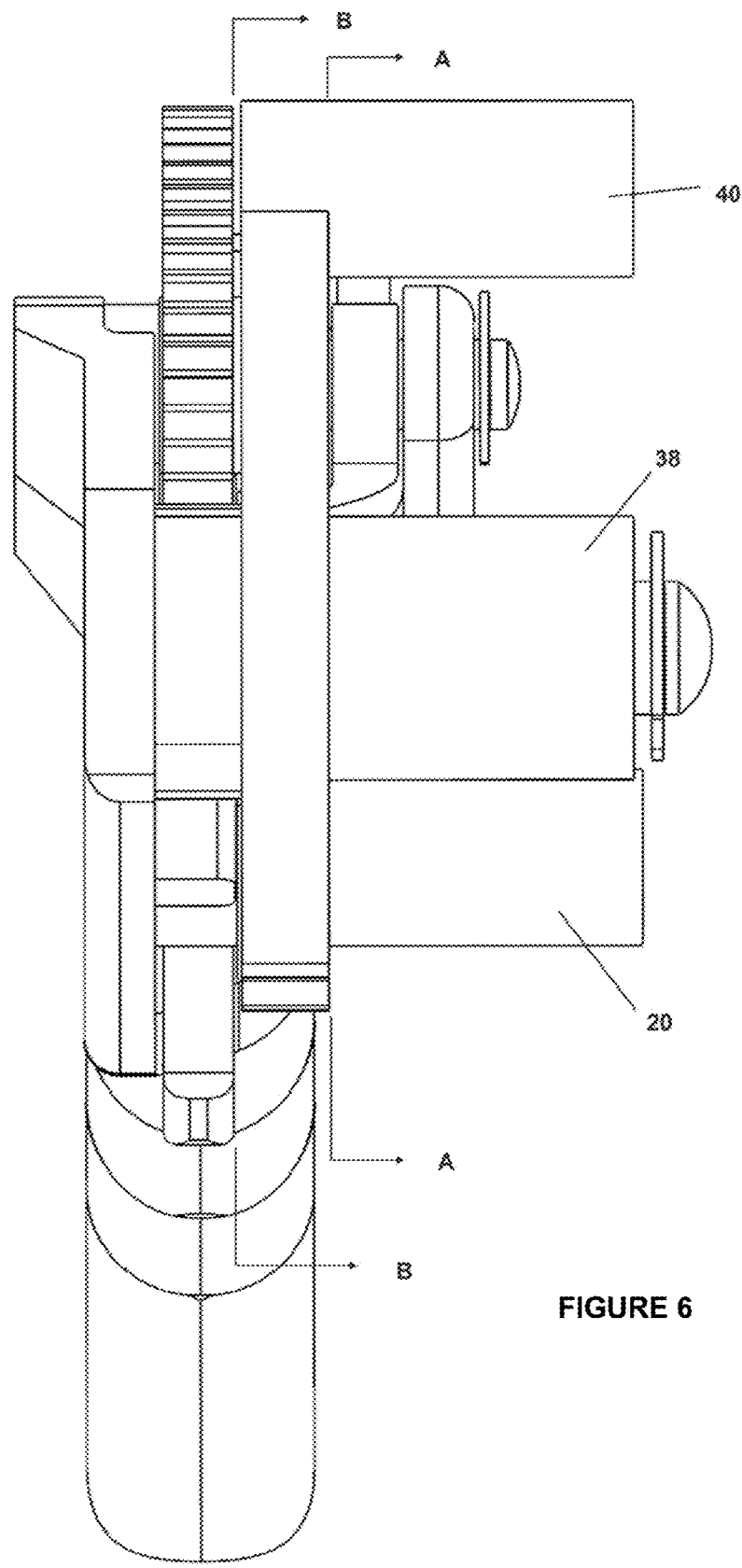

FIGS. 3-6 are side, front, rear, and top views of an exemplary bending instrument as disclosed herein. FIG. 3 is a right side view of the bending instrument. FIG. 4 is a front view of the bending instrument. FIG. 5 is a rear view of the bending instrument. FIG. 6 is a top view of the bending instrument.

Figure 7A:
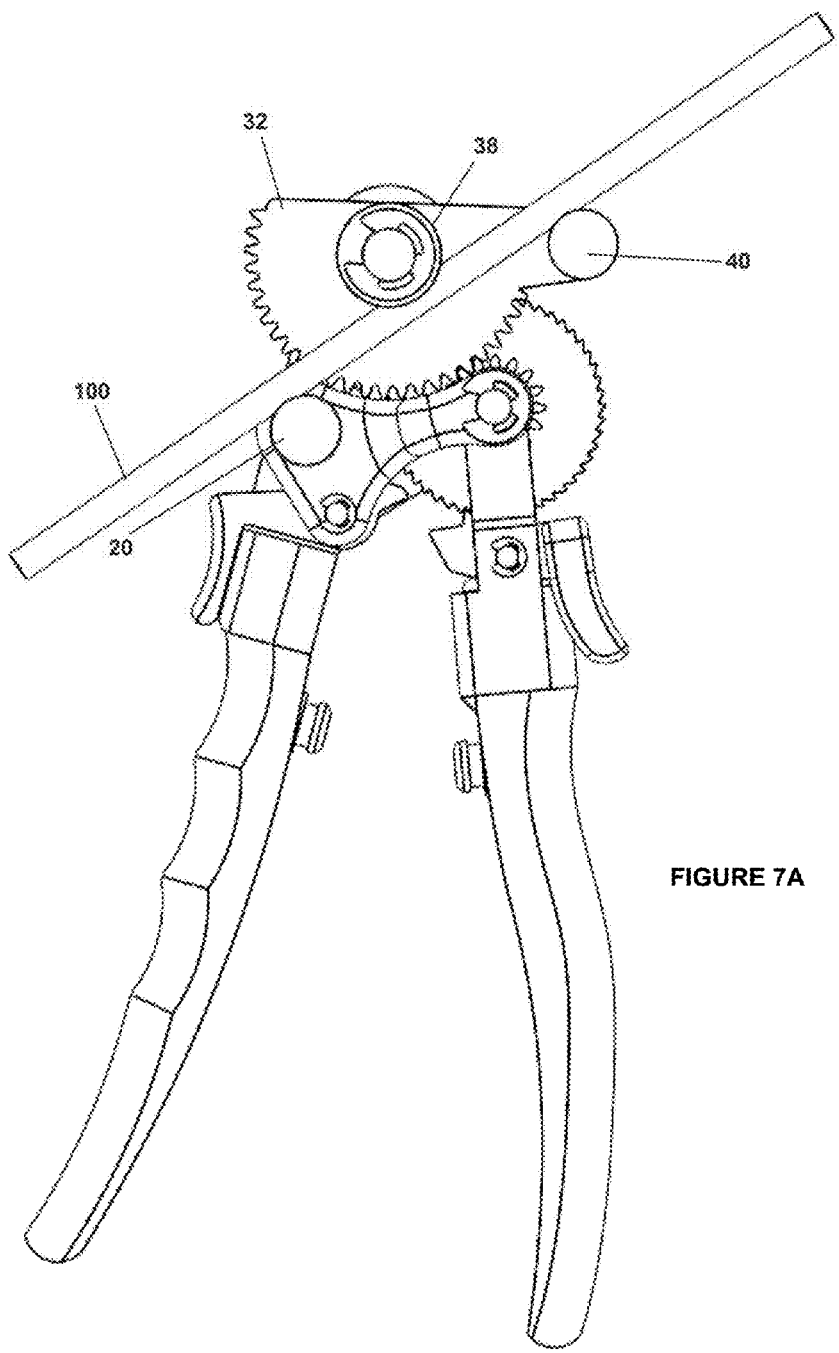
Figure 7B:
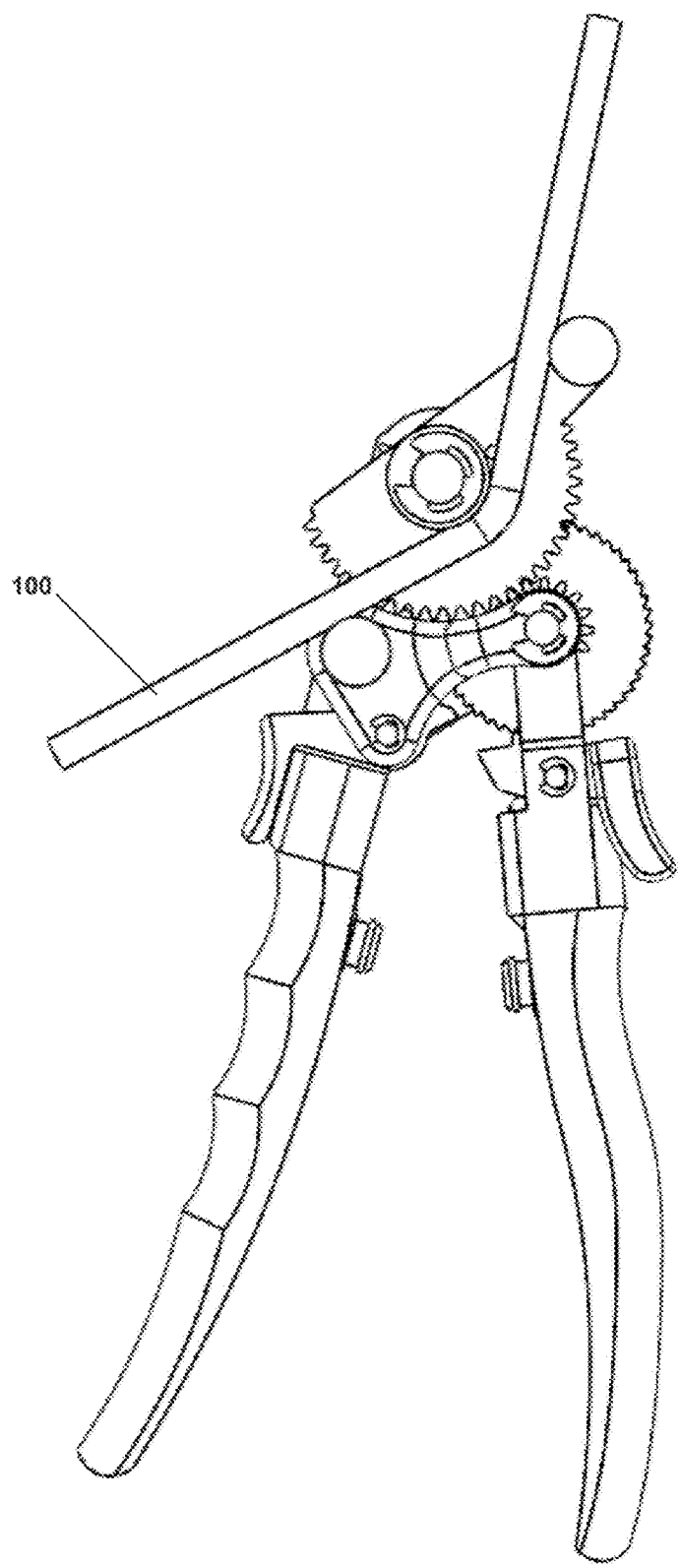
Figure 7C:
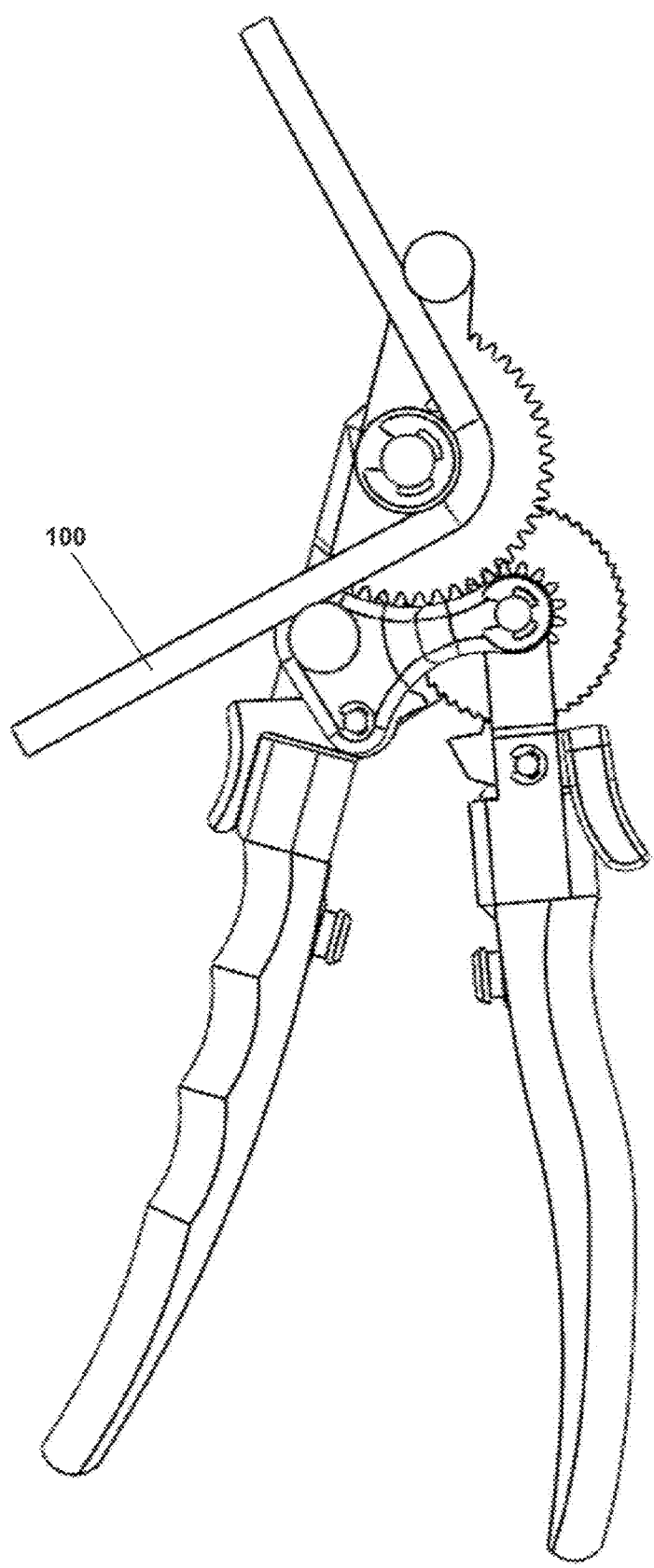

FIGS. 7A-7C depict the bending of a rod using an exemplary bending instrument as disclosed herein. FIG. 7A depicts the rod within an exemplary bending instrument as disclosed herein, prior to bending of the rod. FIG. 7B depicts the rod within the bending instrument, following slight bending of the rod. FIG. 7C depicts the rod within the bending instrument, following further bending of the rod.

Figure 8:
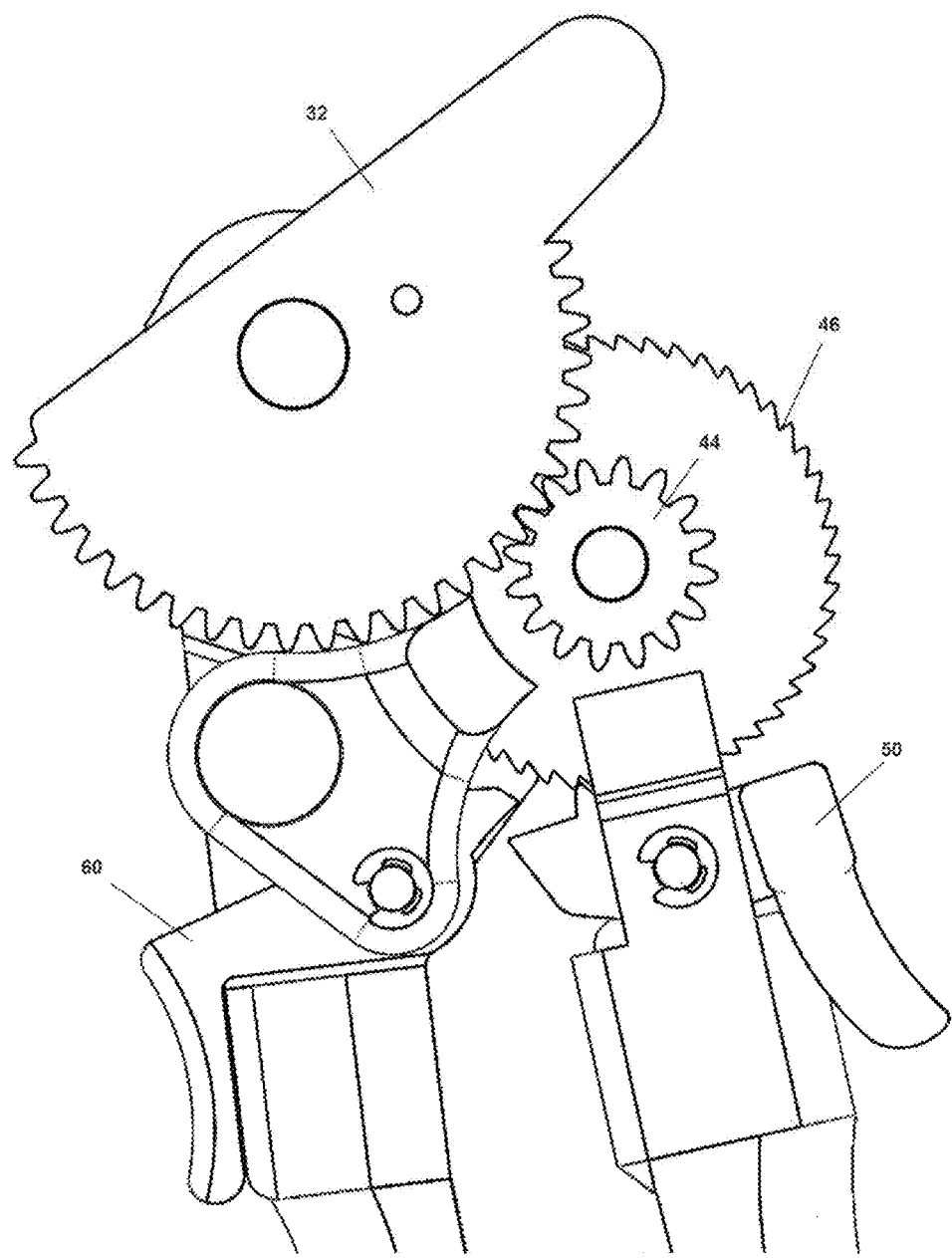

FIG. 8 is an isolated, partially transparent side view of the gear assembly of the bending instrument of FIGS. 3-6, taken along line A-A of FIG. 6.

Figure 9:
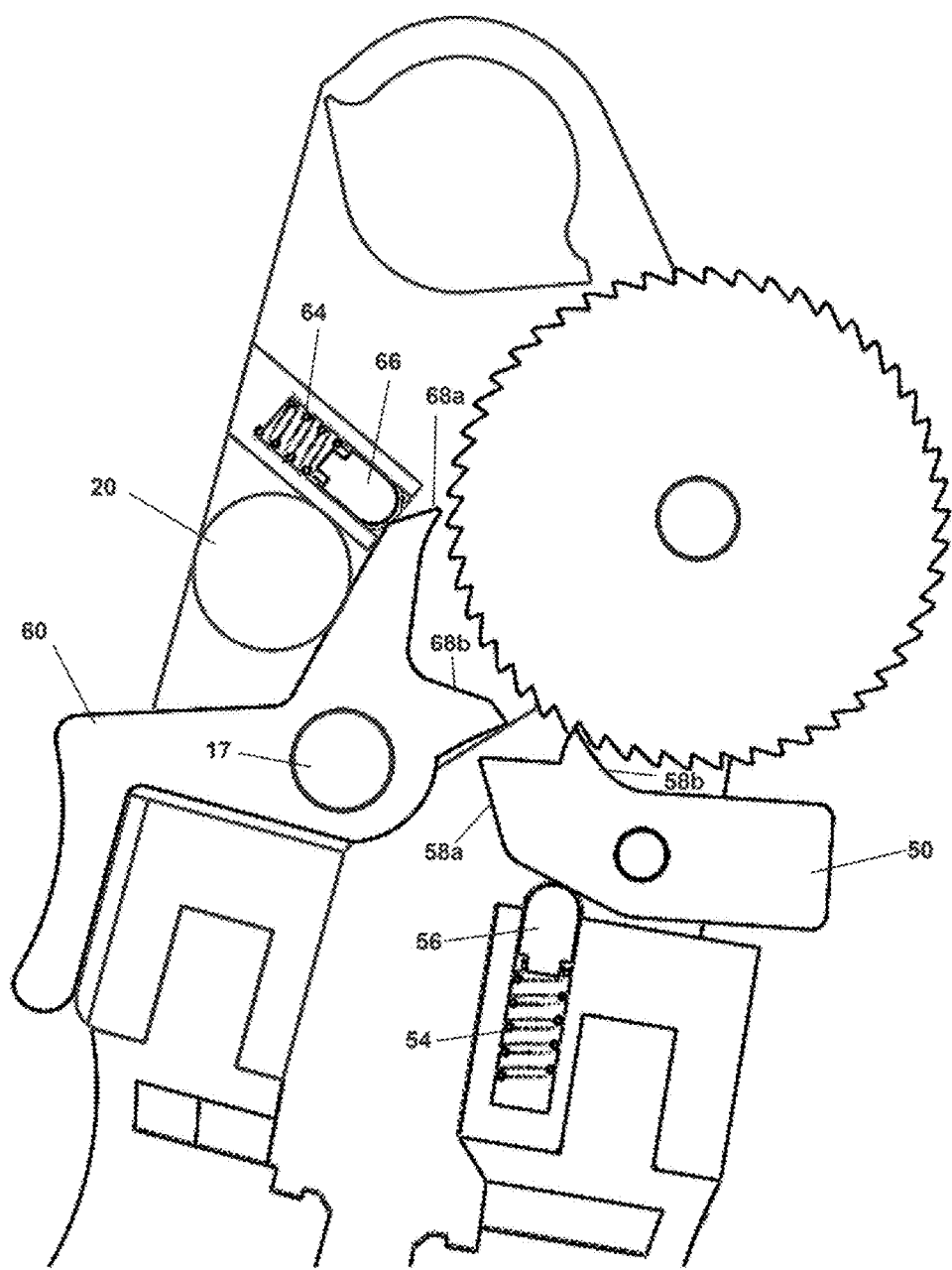

FIG. 9 is an isolated, partially transparent side view of the gear assembly of the bending instrument of FIGS. 3-6, taken along line B-B of FIG. 6.

Figure 10A:
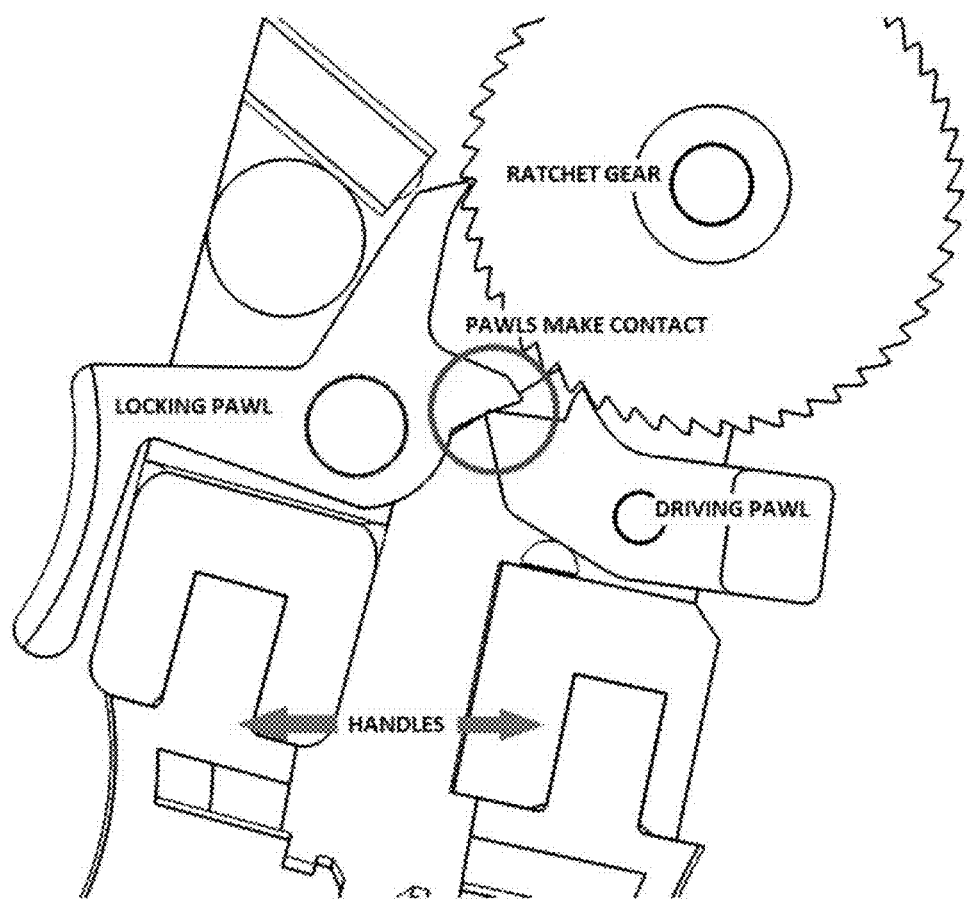
Figure 10B:
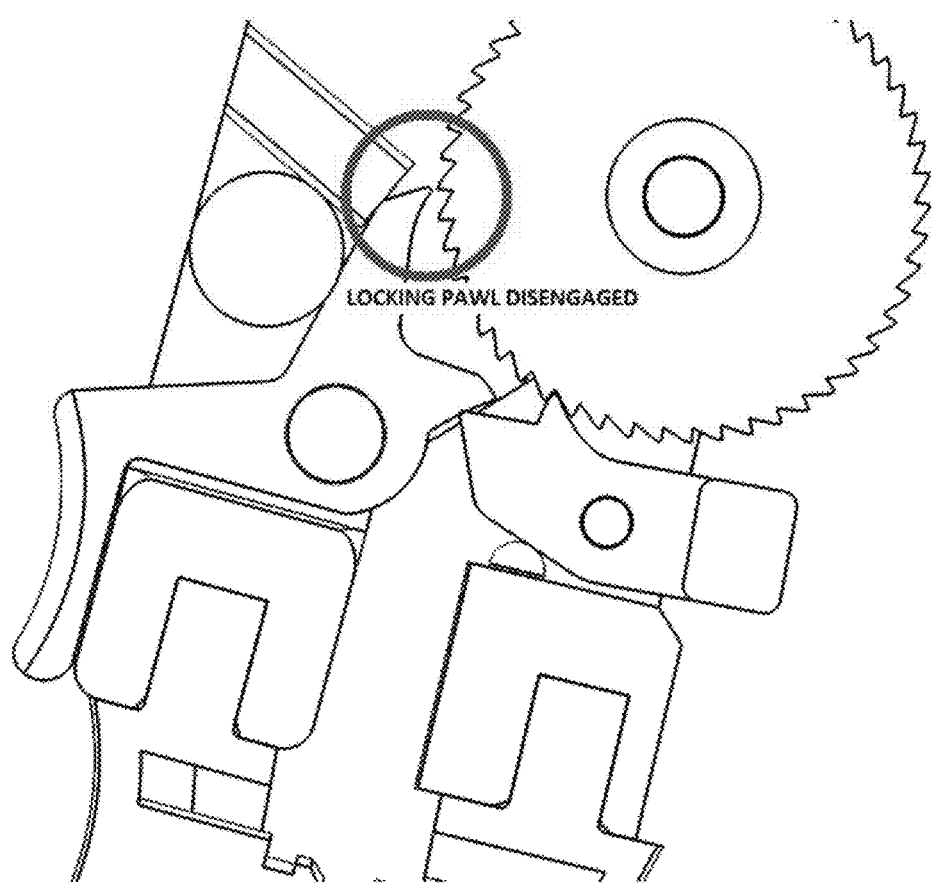
Figure 10C:
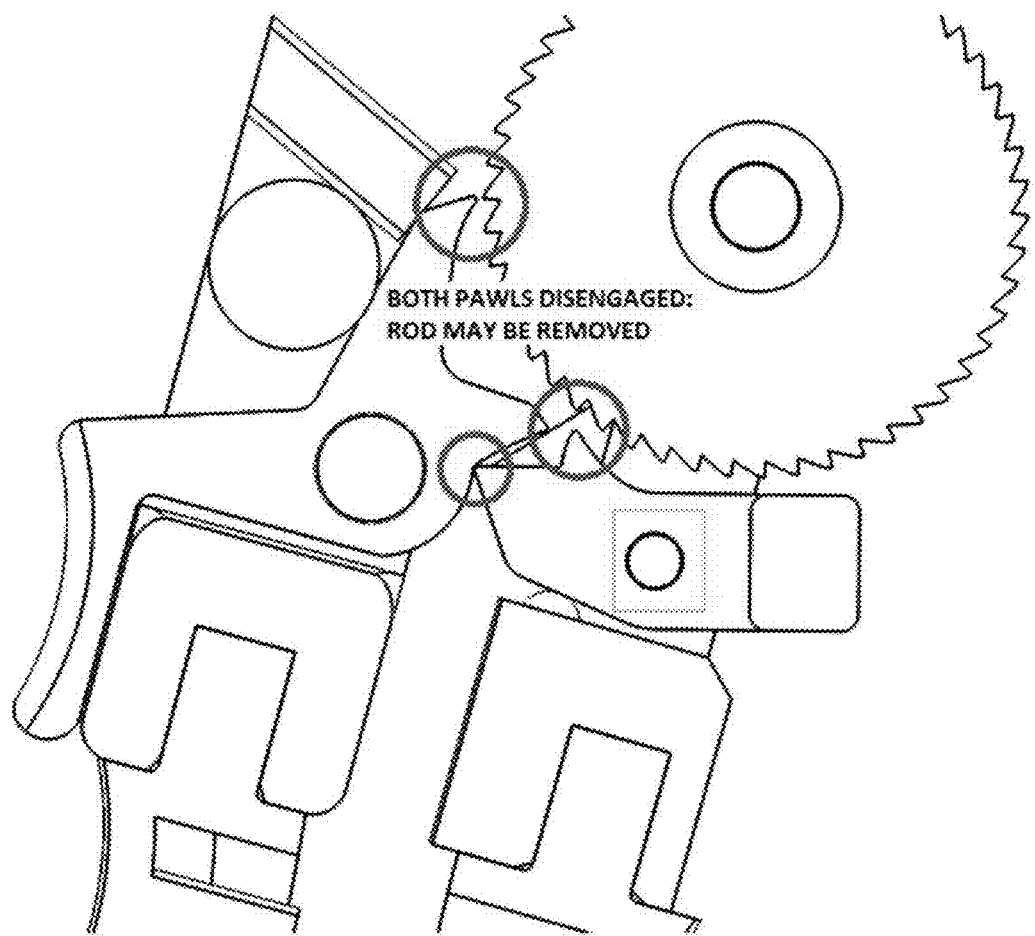

FIGS. 10A-10C depict the operation of the locking and driving pawls of the gear assembly of an exemplary bending instrument as disclosed herein. FIG. 10A depicts the locking and driving pawls in a blocking position. FIG. 10B depicts the locking and driving pawls in a partially disengaged position. FIG. 10C depicts the locking and driving pawls in a fully disengaged position as disclosed herein.

DETAILED DESCRIPTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a bending member" can include two or more such bending members unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

Described herein with reference to FIGS. 1-10C, are bending instruments for selectively applying a bending force to a rod or rod-like element 100, such as for example and without limitation, a surgical rod. In exemplary aspects, a bending instrument 10 can comprise a first handle 12, a second handle 22, and a gear assembly 30. As further disclosed herein, it is contemplated that the bending instrument 10 can provide for improved safety relative to conventional rod benders, while also reducing the duration of rod bending procedures and permitting one-person and/or one-handed bending of a rod. It is further contemplated that the bending instrument 10 can be constructed with a minimal part count to thereby ensure that the bending instrument has a relatively low weight (e.g., less than five pounds, and, more preferably, less than two pounds) and is easily manufactured. It is further contemplated that the bending instrument 10 can be configured to accurately produce small radius bends, as well as gradual bends. In still further aspects, it is contemplated that the bending instrument 10 can comprise fully autoclavable materials. In exemplary surgical applications, it is contemplated that the bending instrument 10 can make the bending of a surgical rod a one-person process, thereby producing increased efficiency in performing a surgical procedure, as well as shorter surgery times. In these applications, it is still further contemplated that the use of the bending instrument 10 during the surgical procedure can lead to a quicker recovery for the patient, as well as a reduced likelihood of infection.

In one aspect, the first handle 12 can have a proximal end 14 and a distal base portion 16. In this aspect, the distal base portion 16 can have a base surface 18 and define first and second support members 20, 21 that project from the base surface. In another aspect, the second handle 22 can have a proximal end 24 and a distal end 26. In this aspect, and with reference to FIGS. 1-2, the distal end 26 of the second handle 22 can be pivotally coupled to the distal base portion 16 of the first handle 12. In exemplary aspects, the distal base portion 16 can further define a projection 19 that is configured to permit pivotal coupling of the second handle 22 to the first handle 12.

In an additional aspect, the gear assembly 30 can comprise a driving gear 32 rotationally coupled to the distal base portion 16 of the first handle 12 and configured for rotation about a first rotational axis 34. In this aspect, and with reference to FIGS. 1-2, the driving gear 32 can have a first surface 36 and can define an inner bending member 38 and an outer bending member 40 that project from the first surface 36 substantially parallel to the first rotational axis 34. Optionally, in exemplary aspects, the inner bending member 38 can define a central opening configured to receive support member 21 of the distal base portion 16 of the first handle 12 such that the inner bending member can rotate about the support member 21. Optionally, it is contemplated that the support member 21 can be configured to apply a spring-biasing force to the driving gear 32.

Figure 2:
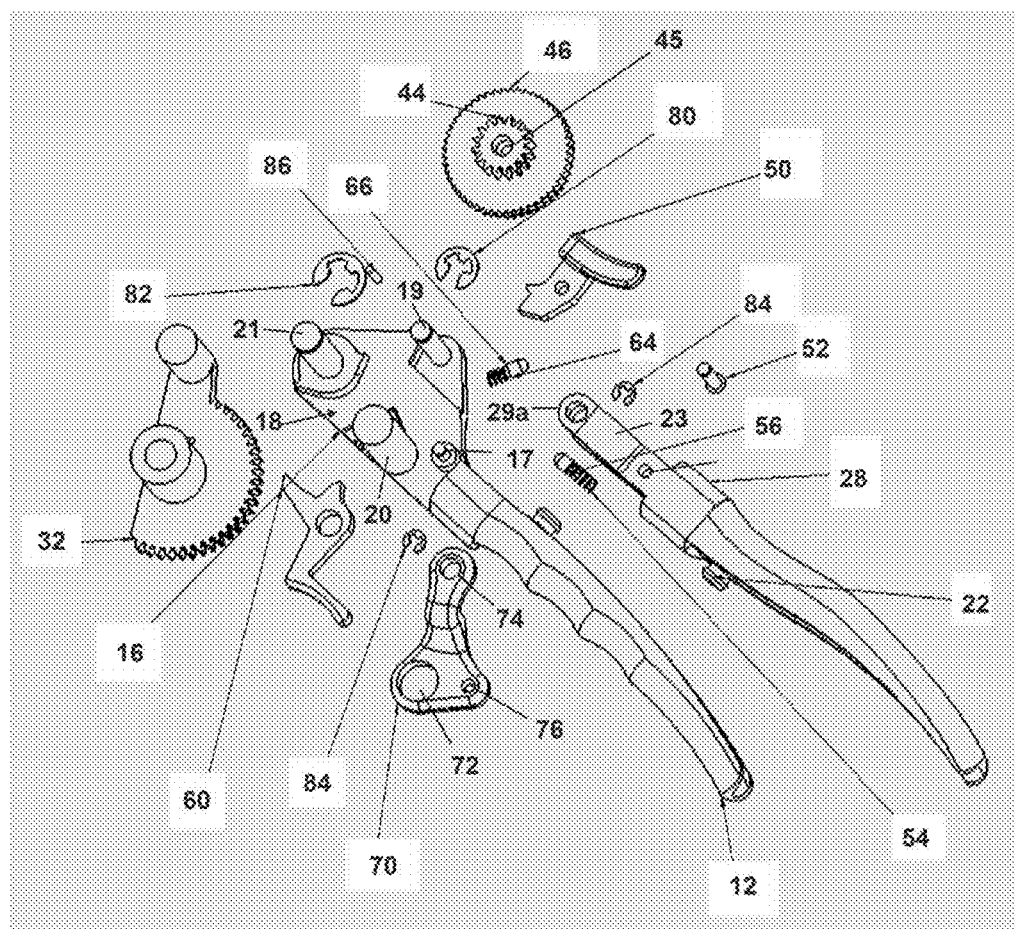
FIG. 2 depicts an exploded perspective view of an exemplary bending instrument as disclosed herein.

In a further aspect, the gear assembly 30 can comprise a compound gear 42 rotationally coupled to the distal base portion 16 of the first handle 12. The compound gear 42 can have a first gear portion 44 and a second gear portion 46 configured for common rotation about a second rotational axis 48, which can optionally be substantially parallel to the first rotational axis 34. As shown in FIG. 2, the second gear portion 46 can be positioned between the distal base portion 16 of the first handle 12 and the first gear portion 44 relative to the second rotational axis 48. In operation, the first gear portion 44 of the compound gear 42 can be positioned in engagement with the driving gear 32. In exemplary aspects, and as shown in FIG. 2, the compound gear 42 can define a central opening 45.

In another aspect, the gear assembly 30 can comprise a driving pawl 50 rotationally coupled to the second handle 22 proximate the distal end 26 of the second handle. In this aspect, the driving pawl 50 can be configured for selective engagement with the second gear portion 46 of the compound gear 42. In use, the driving pawl 50 can be configured for rotation about a rotational axis 55, which can optionally be substantially parallel to the first and second rotational axes 34, 48. As the driving pawl 50 rotates relative to the rotational axis 55, it is contemplated that the driving pawl can effect rotation of the second gear portion 46 of the compound gear 42.

In yet another aspect, the gear assembly 30 can comprise a locking pawl 60 rotationally coupled to the distal base portion 16 of the first handle 12. In this aspect, the locking pawl 60 can be configured for selective engagement with the second gear portion 46 of the compound gear 42 to thereby restrict rotation of the compound gear about the second rotational axis 48. In use, the locking pawl 60 can be configured for rotation about a rotational axis 65, which can optionally be substantially parallel to the first and second rotational axes 34, 48 and the rotational axis of the driving pawl 50. As the driving pawl 50 rotates relative to rotational axis 55 to thereby effect rotation of the second gear portion 46 of the compound gear 42, the locking pawl 60 can be configured to sequentially engage respective teeth defined by the second gear portion as the compound gear rotates.

In exemplary aspects, and with reference to FIG. 7A, the support member 20 of the first handle 12 and the inner and outer bending members 38, 40 of the driving gear 32 can cooperate to define a rod receiving channel 160 configured to receive a rod 100. In these aspects, it is contemplated that pivotal movement of the second handle 22 relative to the first handle 12 (e.g., movement of the second handle from a fully expanded position toward the first handle) can be configured to effect a corresponding movement of the driving pawl 50. It is further contemplated that rotation of the compound gear 42 (effected by rotation of the driving pawl 50) can, in turn, effect rotation of the driving gear 32, which is positioned in engagement with the first gear portion 44 of the compound gear. As shown in FIGS. 7A-7C, rotation of the driving gear 32 can cause movement of the outer bending member 40 about an arcuate path that partially circumferentially surrounds the first rotational axis 34 within a plane perpendicular to the first rotational axis, with the arcuate path having a radius of curvature substantially corresponding to a distance between the first rotational axis and a center point of the outer bending member. Thus, it is contemplated that the outer bending member 40 can apply a bending force to and thereby deform a first portion of the rod 100 relative to a bending point proximate the surface of the inner bending member 38 positioned in engagement with the rod.

Figure 1:
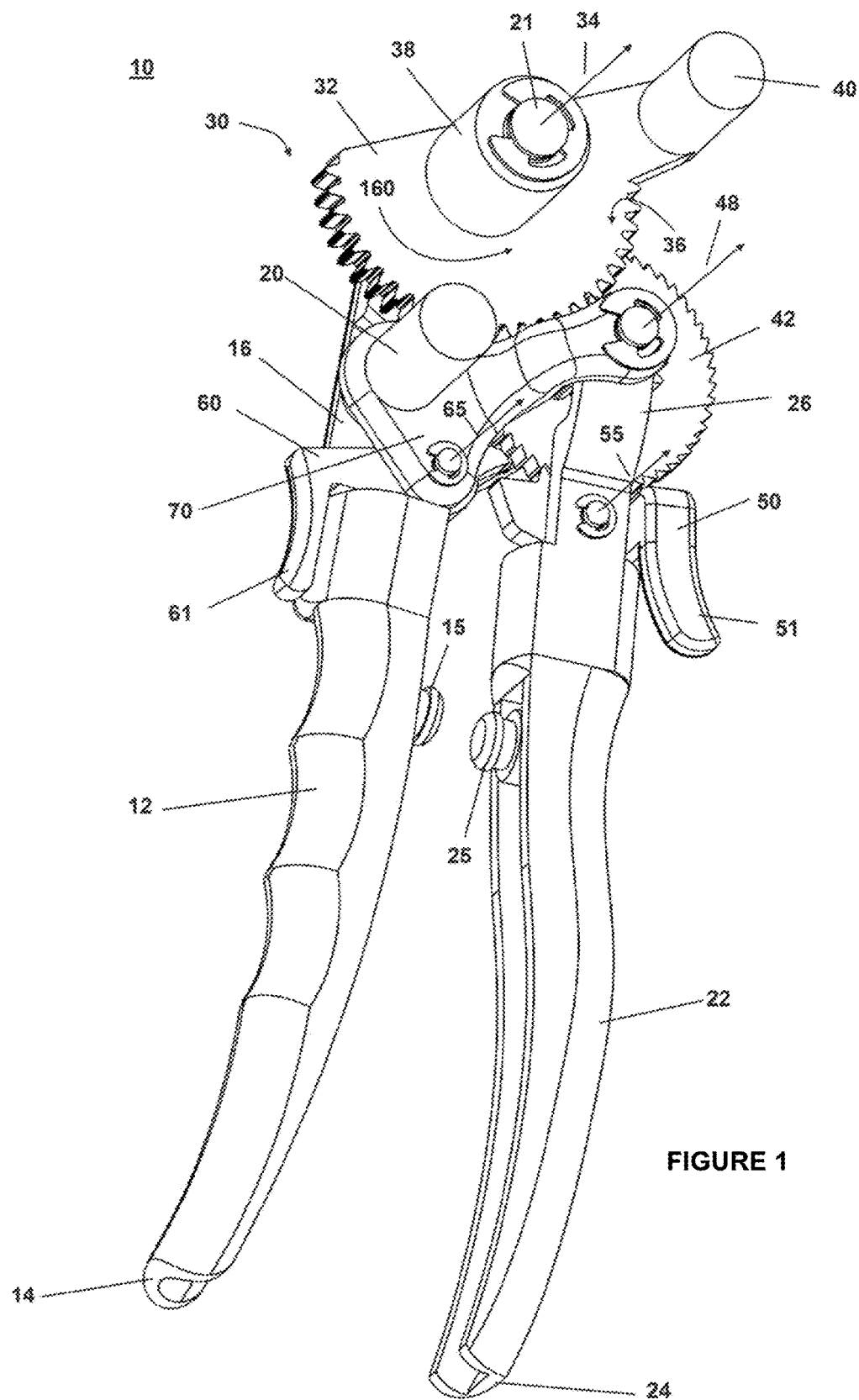
FIG. 1 depicts a perspective view of an exemplary bending instrument as disclosed herein.

In exemplary aspects, as shown in FIGS. 1-2, the distal end 26 of the second handle 22 can optionally define a yoke 23 having a first opening 29*a* configured to receive projection 19 defined by the distal base portion 16. In exemplary aspects, the yoke 23 can have opposed arms 27*a*, 27*b* that are positioned on opposing sides of the compound gear 42, and the projection 19 can be received within both the central opening 45 of the compound gear and the first opening 29*a* of the yoke. In exemplary aspects, the yoke 23 can extend outwardly from an upper driving portion 28 of the second handle 22 that has an increased thickness relative to adjoining portions of the second handle.

In exemplary aspects, the locking pawl 60 can be operatively coupled to the distal base portion 16 of the first handle by a projection 17, as shown in FIGS. 1-2. In these aspects, a center point of the projection 17 can be substantially axially aligned with rotational axis 65. Similarly, it is contemplated that the driving pawl 50 can be operatively coupled to the second handle 22 by a pin 52 that is received within a second opening 29*b* of the yoke 23 of the distal end 26 of the second handle 22. It is further contemplated that the driving pawl 50 can be generally positioned proximate a bottom portion of the compound gear 42.

In exemplary aspects, and as shown in FIGS. 1-2, the bending instrument 10 can comprise a support plate 70 that is configured to receive the support member 20, the projection 17 passing through the locking pawl 60, and the projection 19 positioned within the first opening 29*a* of the yoke 23 of the distal end 26 of the second handle 22 (and also positioned within the central opening 45 of the compound gear 42). In these aspects, it is contemplated that the support plate 70 can optionally define an opening 72 configured to receive the support member 20, an opening 74 configured to receive the projection 19 positioned within the first opening 29*a* of the yoke 23, and an opening 76 configured to receive the projection 17 passing through the locking pawl 60.

In one exemplary aspect, the first and second gear portions 44, 46 of the compound gear 42 can have respective diameters, and the diameter of the first gear portion can be less than the diameter of the second gear portion. In this aspect, it is contemplated that rotation of the second gear portion 46 results in a corresponding rotation of the first gear portion 44. In further aspects, the driving gear 32 can have a toothed portion. In these aspects, the first gear portion 44 of the compound gear 42 can be configured to impart a rotational force to the driving gear 32. It is contemplated that the first gear portion 44 of the compound gear 42 and the driving gear 32 have a gear ratio of at least 2:1 or, more preferably, of at least 3:1. In exemplary aspects, the gear ratio can be configured to vary throughout the motion of the gear assembly in accordance with a desired gear ratio profile. In these aspects, it is contemplated that the use of a large lever arm as disclosed herein, in combination with the gear ratio, can yield a substantial mechanical advantage. For example, it is contemplated that an input squeezing force applied to the handles as disclosed herein can produce an output bending force on the rod element that is greater than the input force, with the mechanical advantage corresponding to the factor by which the input force is amplified or multiplied to equal the output bending force. In exemplary non-limiting aspects, with a 3:1 gear ratio, it is contemplated that a mechanical advantage of greater than 9× (e.g., about 9.6×) can be produced. However, it is contemplated that other mechanical advantages (higher and lower) can be achieved. In further exemplary aspects, it is contemplated that the gear design disclosed herein can provide a substantially constant angular displacement throughout a squeezing action. In still further exemplary aspects, it is contemplated that each completed squeezing action can correspond to a desired bend of a rod element (for example and without limitation, about 7.5 degrees per complete squeeze), with each squeezing action corresponding to an advancement of a desired number of ratchet teeth (e.g., two or three teeth). Thus, it is contemplated that each advancement over a respective ratchet tooth can correspond to a particular angular bend of a rod element (e.g., about 2.5 degrees), yielding an indication of the bending resolution of the bending instrument.

In operation, the gear assembly 30 can be configured to be positioned in a plurality of operational positions by selective advancement of the second handle 22 relative to the first handle 12. In exemplary aspects, the plurality of operational positions can comprise a rotational position, a partially disengaged position, and a fully disengaged position. As shown in FIGS. 7A-9, in the rotational position, it is contemplated that the driving pawl 50 and the locking pawl 60 can be positioned in engagement with the second gear portion 46 of the compound gear 42. As shown in FIG. 10A, in additional exemplary aspects, in the rotational position, the advancement of the driving pawl 50 (through movement of the second handle 22) can effect rotation of the second gear portion 46, and the locking pawl 60 can be positioned to sequentially engage adjacent teeth of the second gear portion. When advancement of the driving pawl 50 has been completed (corresponding to reaching a limit, such as a mechanical stop, or otherwise ending a squeezing action by which the second handle 22 is advanced relative to the first handle 12), the locking pawl 60 can be configured to maintain engagement with a tooth of the second gear portion 46 and to prevent counter-rotation (reverse rotation in an opposite direction from the rotation generated by the driving pawl) of the compound gear until the gear assembly 30 is positioned in the partially disengaged position as further disclosed herein.

Thus, after reaching the limit or otherwise ending the squeezing action, the first and second handles 12, 22 can be released to return to a fully expanded position while the locking pawl maintains engagement with the second gear portion 46. In exemplary aspects, at least the second handle (and, optionally, the first and second handles) can be biased to the fully expanded position, which can correspond to the maximum separation between the first and second handles. From the fully expanded position, it is contemplated that the second handle 22 can again be advanced relative to the first handle 12 (e.g., by squeezing action) to effect further advancement of the driving pawl 50 (and further rotation of the second gear portion 46), and this sequence can be repeated until the gear assembly 30 is positioned in the partially disengaged position as further disclosed herein.

Optionally, in some aspects, and with reference to FIG. 1, the driving pawl 50 and the locking pawl 60 can each define respective gripping elements 51, 61. In these aspects, it is contemplated that the gripping elements 51, 61 can project outwardly from the pawls 50, 60 such that they are easily engageable by one or more fingers of a user during use of the bending instrument 10. For example, as shown in FIG. 1, it is contemplated that the gripping elements 51, 61 can be positioned outwardly of the respective handles 12, 22. Alternatively, it is contemplated that the gripping elements 51, 61 can project toward the user of the bending instrument 10. In use, it is contemplated that the gripping element 51 can be selectively engaged by a user to permit manual disengagement of the driving pawl 50 from the compound gear 42. Similarly, it is contemplated that the gripping element 61 can be selectively engaged by a user to permit manual disengagement of the locking pawl 60 from the compound gear 42. In exemplary aspects, it is contemplated that the gripping element 51 can be configured for engagement by a thumb of a user, whereas the gripping element 61 can be configured for engagement by an index finger of the user. In use, it is contemplated that the gripping elements 51, 61 can be used to selectively disengage at least one of the driving pawl 50 and the locking pawl 60 from the second gear portion of the compound gear and to subsequently selectively re-engage at least one of the driving pawl and the locking pawl with the second gear portion of the compound gear.

Optionally, in additional aspects, and with reference to FIG. 9, the locking pawl 60 can define a first finger element 68a and a second finger element 68b. In these aspects, it is contemplated that the driving pawl 50 can optionally define a first finger element 58a and a second finger element 58b. In the rotational position, the first finger element 68a of the locking pawl 60 can be positioned in engagement with the second gear portion 46 of the compound gear 42, the second finger element 68b of the locking pawl 60 can be spaced from the first finger portion 58a of the driving pawl 50, and the second finger portion 58b of the driving pawl 50 can be positioned in engagement with the second gear portion 46 of the compound gear 42. Although disclosed herein as finger elements 58a, 58b, 68a, 68b, it is contemplated that the engagement surfaces of the driving and locking pawls 50, 60 can have any shape or surface features that permits engagement as disclosed herein.

As shown in FIGS. 2 and 8-9, the first and second handles 12, 22 can define respective receptacles that are configured to receive respective plunger heads 56, 66. In exemplary aspects, the receptacles can also receive respective plunger springs 54, 64 that surround a lower portion of the plunger heads and are configured to bias the plunger springs to a deployed position. In further exemplary aspects, the plunger heads 56, 66 can be positioned in engagement with the driving and locking pawls 50, 60 to help support engagement of the pawls with the gear assembly, while minimizing inadvertent disengagement of the pawls from the gear assembly. It is contemplated that the plunger heads 56, 66 can have a top, dome-shaped portion that is configured to provide smooth and/or minimal contact with the driving and locking pawls 50, 60, thereby producing less wear on the plunger heads and driving and locking pawls.

In operation, and with reference to FIGS. 10A-10B, it is contemplated that the gear assembly 30 can be positioned in the partially disengaged position following continued advancement of the second handle 22 relative to the first handle 12. As shown in FIG. 10A, as the second handle 22 continues to advance toward the first handle 12, the first finger portion 58a of the driving pawl 50 contacts a portion of the second finger portion 68b of the locking pawl 60. As further described below, continued movement of the second handle 22 toward the first handle 12 moves the gear assembly to the partially disengaged position and, eventually, to the fully disengaged position. Optionally, in exemplary aspects, and with reference to FIG. 10B, in the partially disengaged position, the first finger portion 68a of the locking pawl 60 can be positioned such that it is not in contact with the compound gear 42, the first finger portion 58a of the driving pawl 50 can be positioned in engagement with the second finger portion 68b of the locking pawl 60, and the second finger portion 58b of the driving pawl 50 can be positioned in engagement with the second gear portion 46 of the compound gear 42. Thus, in the partially disengaged position, the locking pawl 60 can be spaced from the second gear portion 46 such that the locking pawl does not actively bear the load of the second gear portion. In contrast, in the partially disengaged position, the driving pawl 50 can remain at least partially seated within the teeth of the second gear portion 46 and therefore, under load. As shown in FIG. 10B, the locking pawl can be limited by a stop, such as, for example, a spring plunger housing as further disclosed herein.

As shown in FIG. 10C, it is further contemplated that the gear assembly 30 can be positioned in the fully disengaged position following continued advancement (e.g., squeezing) of the second handle 22 relative to the first handle 12 after the gear assembly is positioned in the partially disengaged position (see FIG. 10B). Optionally, in exemplary aspects, in the fully disengaged position, the driving pawl 50 can be positioned in engagement with the locking pawl 60 and the driving and locking pawls can be positioned such that they are not in contact with the compound gear 42, thereby permitting removal of a rod from the rod receiving channel 160. In exemplary aspects, the fully disengaged position can correspond to a minimum separation distance between the first and second handles 12, 22. It is contemplated that the continued driving of the second handle 22 toward the first handle 12 can cause a moment about the driving pawl 50 that disengages the driving pawl from the second gear portion 46 of the compound gear 42. It is still further contemplated that, following disengagement of the driving pawl 50 from the second gear portion 46, the gear assembly 30 can experience some amount of "springback," resulting from the loading of the gear assembly 30 by the spring force in the spinal rod. In further exemplary aspects, it is contemplated that, while the gear assembly 30 is positioned in the disengaged position, the first and second handles 12, 22 can be moved apart without transmitting load to the second gear portion 46 of the compound gear 42.

In exemplary aspects, it is contemplated that the locking pawl 60 can limit rod "springback" and permit release of the second handle 22 so that another sequential "squeezing"

cycle can begin (by advancement of the second handle relative to the first handle 12). The release of the second handle 22 can occur following "over-squeezing" of the second handle during the last few degrees of handle movement. It is contemplated that, during this "over-squeezing" action, the locking and driving pawls 60, 50 can contact each other such that both pawls are disengaged from the second gear portion 46 of the compound gear 42 and thereby positioned in the fully disengaged position as disclosed herein. It is still further contemplated that the release of the second handle 22 and resetting of the engagement among the locking and driving pawls 60, 50 and the second gear portion 46 can be performed in a single-handed manner.

Thus, as disclosed in detail above, it is contemplated that the gear assembly of the bending instrument 10 can be configured to preserve bending progress, with the driving pawl applying force to the ratchet gear, which in turn bends the rod, and the locking pawl inhibiting rod "springback" and allowing the handle to be released for the next sequential squeezing action.

Optionally, in exemplary aspects, the driving gear 32 and the first gear portion 44 of the compound gear 42 can have respective teeth that have an involute tooth form as is known in the art. In these aspects, it is contemplated that the involute tooth profile can promote even wearing of the gear teeth from base to tip as the gears rotate, thereby reducing stress on the gear and prolonging gear life. It is further contemplated that the involute tooth profile can be advantageous for permitting interaction between gears of different sizes. Optionally, in other exemplary aspects, it is contemplated that the second gear portion 46 of the compound gear 42 can have conventional ratchet teeth as are known in the art.

As shown in FIG. 1, it is contemplated that the first and second handles 12, 22 can be provided with ergonomic grip features to provide improved stability, control, and comfort for users of the bending instrument. For example, in one aspect, it is contemplated that outer portions of the first and second handles 12, 22 can be shaped to conform to portions of a user's hands. It is further contemplated that at least one of the first and second handles 12, 22 can define a projecting portion that is configured to prevent inadvertent sliding of a user's hand relative to the handles.

In further exemplary aspects, inner portions of the first and second handles 12, 22 can optionally define respective engagement portions 15, 25 that are configured for operative engagement with a spring (not shown), such as, for example and without limitation, a double leaf spring or a barrel spring as are known in the art. In these aspects, the spring can be configured to apply positive pressure to the hand of a user as the first and second handles 12, 22 approach one another. It is contemplated that the spring can be configured to at least partially compress within itself as the first and second handles 12, 22 approach one another.

Generally, it is contemplated that the bending instrument 10 can comprise one or more E-clips (see FIG. 2, for example, showing E-clips 80, 82, 84) or other fastening elements to maintain operative coupling between the components of the instrument. In exemplary aspects, the E-clips can be configured to engage and surround a portion of a pin (e.g., pin 52) or a support member (e.g., support member 21) as further disclosed herein.

In exemplary aspects, it is contemplated that the bending instrument 10 can comprise stainless steel materials, such as, for example and without limitation, 465 Stainless Steel or 17-4 PH Stainless Steel as are known in the art.

In use, it is contemplated that the bending instruments disclosed herein can be used to selectively bend any conventional rod-like element, including, for example and without limitation, a surgical rod. It is further contemplated that the disclosed bending instruments can achieve a compound mechanical advantage not found in conventional rod benders. More particularly, it is contemplated that the second handle 22, which is not directly coupled to the driving gear 32, can have a compound mechanical advantage that lessens the grip force required to apply the bending force to a rod.

It is further contemplated that the compound gear 42 disclosed herein can allow the gear assembly 30 to have a finely controlled locking mechanism by maximizing the rotation of the compound gear 42 (i.e., the number of "clicks") for each sequential cycle of advancement of the second handle 22 relative to the first handle 12. In exemplary aspects, it is contemplated that each sequential cycle of advancement of the second handle 22 (i.e., each complete "squeeze") can correspond to at least three "clicks" that are produced by the teeth of the second gear portion 46 of the compound gear 42 passing over the locking pawl 60. It is further contemplated that the number and profile of the teeth of the first and second gear portions 44, 46 and/or the driving gear 32 can be selectively varied to alter the relative rotation of the driving gear 32 during each respective "squeeze" of the handles.

In exemplary applications, a user of the bending instrument 10 can operate the instrument using his or her right hand while controlling the position of a rod-like element using his or her left hand. In these applications, it is contemplated that the range of the handles of the bending instrument can be configured to fit the hand of an average person. In exemplary aspects, it is contemplated that the bending instrument can be opened and reset using one hand. In further exemplary aspects, it is contemplated that the bending instrument can be configured to minimize the number of locations where pinching of gloves is possible.

Although generally described herein with reference to a right-handed user, it is contemplated that the disclosed bending instrument 10 can be configured for a left-handed user by mirroring the configuration of the components of the instrument such that the user can operated the instrument with his or her left hand and control the position of a rod-like element with his or her right hand.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A bending instrument comprising:
    a first handle having a proximal end and a distal base portion, the distal base portion having a base surface and defining a support member that projects from the base surface;
    a second handle having a proximal end and a distal end, the distal end being pivotally coupled to the distal base portion of the first handle; and
    a gear assembly comprising:
        a driving gear rotationally coupled to the distal base portion of the first handle and configured for rotation about a first rotational axis, the driving gear having a first surface and defining an inner bending member and an outer bending member that project from the first surface substantially parallel to the first rotational axis;
a compound gear rotationally coupled to the distal base portion of the first handle and having a first gear portion and a second gear portion, the compound gear configured for common rotation about a second rotational axis, wherein the second gear portion is positioned between the distal base portion of the first handle and the first gear portion relative to the second rotational axis, and wherein the first gear portion is positioned in engagement with the driving gear;
a driving pawl pivotally coupled to the second handle proximate the distal end of the second handle, the driving pawl being configured for selective engagement with the second gear portion of the compound gear; and
a locking pawl pivotally coupled to the distal base portion of the first handle and configured for selective engagement with the second gear portion of the compound gear to thereby prevent rotation of the compound gear about the second rotational axis,
wherein the support member of the first handle and the inner and outer bending members of the driving gear cooperate to define a rod receiving channel configured to receive a rod, wherein pivotal movement of the second handle relative to the first handle is configured to effect a corresponding pivotal movement of the driving pawl, and wherein the driving pawl is configured to effect rotation of the compound gear to thereby rotate the driving gear.

2. The bending instrument of claim 1, wherein the first and second gear portions have respective diameters, wherein the diameter of the first gear portion is less than the diameter of the second gear portion, and wherein rotation of the second gear portion results in a corresponding rotation of the first gear portion.

3. The bending instrument of claim 2, wherein the driving gear has a toothed portion, wherein the first gear portion of the compound gear is configured to impart a rotational force to the driving gear, and wherein the first gear portion of the compound gear and the driving gear have a gear ratio of at least 2:1.

4. The bending instrument of claim 2, wherein the driving gear has a toothed portion, wherein the first gear portion of the compound gear is configured to impart a rotational force to the driving gear, and wherein the first gear portion of the compound gear and the driving gear have a gear ratio of at least 3:1.

5. The bending instrument of claim 3, wherein the gear ratio is configured to vary throughout motion of the gear assembly.

6. The bending instrument of claim 1, wherein the gear assembly is configured to be positioned in a plurality of operational positions by selective advancement of the second handle relative to the first handle, wherein the plurality of operational positions comprise a rotational position, a partially disengaged position, and a fully disengaged position, wherein, in the rotational position, the driving pawl and the locking pawl are positioned in engagement with the second gear portion of the compound gear.

7. The bending instrument of claim 6, wherein, prior to advancement of the second handle relative to the first handle the first and second handles are in a fully expanded position, wherein, in the rotational position, the locking pawl is configured to maintain the rotational position of the second gear portion of the compound gear when a limit of the advancement of the second handle is reached, and wherein, upon reaching the limit of the advancement of the second handle, the first and second handles are configured to return to the fully expanded position, from which the second handle can be further selectively advanced relative to the first handle.

8. The bending instrument of claim 6, wherein the locking pawl defines a first finger element and a second finger element, wherein the driving pawl defines a first finger element and a second finger element, and wherein, in the rotational position, the first finger element of the locking pawl is positioned in engagement with the second gear portion of the compound gear, the second finger element of the locking pawl is spaced from the first finger element of the driving pawl, and the second finger portion of the driving pawl is positioned in engagement with the second gear portion of the compound gear.

9. The bending instrument of claim 8, wherein the gear assembly is positioned in the partially disengaged position following continued advancement of the second handle relative to the first handle after the gear assembly is positioned in the rotational position, and wherein, in the partially disengaged position, the first finger portion of the locking pawl is not in contact with the compound gear, the first finger portion of the driving pawl is positioned in engagement with the second finger portion of the locking pawl, and the second finger portion of the driving pawl is positioned in engagement with the second gear portion of the compound gear.

10. The bending instrument of claim 9, wherein the gear assembly is positioned in the fully disengaged position following continued advancement of the second handle relative to the first handle after the gear assembly is positioned in the partially disengaged position, and wherein, in the fully disengaged position, the driving pawl is positioned in engagement with the locking pawl and the driving and locking pawls are not in contact with the compound gear, thereby permitting removal of a rod from the rod receiving channel.

11. The bending instrument of claim 10, wherein the fully disengaged position corresponds to a minimum separation distance between the first and second handles.

12. The bending instrument of claim 1, wherein the driving pawl comprises a gripping element configured to permit selective manual disengagement of the driving pawl from the second gear portion of the compound gear, and wherein the locking pawl comprises a gripping element configured to permit selective manual disengagement of the locking pawl from the second gear portion of the compound gear.

13. A method of bending a rod, comprising:
positioning the rod within a rod receiving channel of a bending instrument, the bending instrument comprising:
a first handle having a proximal end and a distal base portion, the distal base portion having a base surface and defining a support member that projects from the base surface;
a second handle having a proximal end and a distal end, the distal end being pivotally coupled to the distal base portion of the first handle; and
a gear assembly comprising:
a driving gear rotationally coupled to the distal base portion of the first handle and configured for rotation about a first rotational axis, the driving gear having a first surface and defining an inner bending member and an outer bending member that project from the first surface substantially parallel to the first rotational axis;

a compound gear rotationally coupled to the distal base portion of the first handle and having a first gear portion and a second gear portion, the compound gear configured for common rotation about a second rotational axis, wherein the second gear portion is positioned between the distal base portion of the first handle and the first gear portion relative to the second rotational axis, and wherein the first gear portion is positioned in engagement with the driving gear;

a driving pawl pivotally coupled to the second handle proximate the distal end of the second handle, the driving pawl being configured for selective engagement with the second gear portion of the compound gear; and a locking pawl pivotally coupled to the distal base portion of the first handle and configured for selective engagement with the second gear portion of the compound gear to thereby prevent rotation of the compound gear about the second rotational axis, wherein the support member of the first handle and the inner and outer bending members of the driving gear cooperate to define the rod receiving channel; and selectively pivotally moving the second handle relative to the first handle to effect a corresponding pivotal movement of the driving pawl, wherein the pivotal movement of the driving pawl effects rotation of the compound gear to thereby rotate the driving gear, wherein the rotation of the driving gear causes movement of the outer bending member along an arcuate path, and wherein the movement of the outer bending member applies a bending force to the rod.

14. The method of claim 13, further comprising selectively adjusting a gear ratio of the first gear portion of the compound gear and the driving gear, wherein the gear ratio is selectively adjusted depending upon one or more characteristics of the rod.

15. The method of claim 13, wherein the step of selectively pivotally moving the second handle comprises selectively disengaging at least one of the driving pawl and the locking pawl from the second gear portion of the compound gear and selectively re-engaging at least one of the driving pawl and the locking pawl with the second gear portion of the compound gear.

16. The method of claim 13, further comprising using the gear assembly to provide a compound mechanical advantage during pivotal movement of the second handle relative to the first handle.

17. The method of claim 13, further comprising advancing the second handle relative to the first handle to position the gear assembly in a rotational position, wherein, in the rotational position, the driving pawl and the locking pawl are positioned in engagement with the second gear portion of the compound gear.

18. The method of claim 17, wherein the locking pawl defines a first finger element and a second finger element, wherein the driving pawl defines a first finger element and a second finger element, and wherein the step of advancing the second handle relative to the first handle to position the gear assembly in the rotational position comprises:

positioning the first finger element of the locking pawl in engagement with the second gear portion of the compound gear;

spacing the second finger element of the locking pawl from the first finger element of the driving pawl; and positioning the second finger portion of the driving pawl in engagement with the second gear portion of the compound gear.

19. The method of claim 18, further comprising continually advancing the second handle relative to the first handle after the gear assembly is positioned in the rotational position until the gear assembly is positioned in a partially disengaged position, wherein, in the partially disengaged position, the first finger portion of the locking pawl is not in contact with the compound gear, the first finger portion of the driving pawl is positioned in engagement with the second finger portion of the locking pawl, and the second finger portion of the driving pawl is positioned in engagement with the second gear portion of the compound gear.

20. The method of claim 19, further comprising continually advancing the second handle relative to the first handle after the gear assembly is positioned in the partially disengaged position until the gear assembly is positioned in a fully disengaged position, and wherein, in the fully disengaged position, the driving pawl is positioned in engagement with the locking pawl and the driving and locking pawls are not in contact with the compound gear, thereby permitting removal of the rod from the rod receiving channel.

* * * * *